United States Patent [19]

Teed

[11] 3,984,272

[45] Oct. 5, 1976

[54] METHOD AND APPARATUS FOR SUCCESSIVELY FORMING DISPOSABLE DIAPERS

[75] Inventor: Richard K. Teed, Greenwood, S.C.

[73] Assignee: Riegel Textile Corporation, New York, N.Y.

[22] Filed: July 25, 1974

[21] Appl. No.: 491,793

[52] U.S. Cl. ............................. 156/201; 156/204; 156/213; 156/291; 156/467; 156/548; 156/522; 156/552
[51] Int. Cl.² ......................................... B31F 1/00
[58] Field of Search ........... 156/522, 552, 548, 291, 156/556, 578, 201, 204, 378, 213, 504, 467; 128/284, 287, 290 R, 296; 19/144.5; 53/61 R

[56] References Cited
UNITED STATES PATENTS

| | | | |
|---|---|---|---|
| 3,382,530 | 5/1968 | Glesner | 156/578 X |
| 3,578,155 | 5/1971 | Small | 128/287 X |
| 3,586,000 | 6/1971 | Ness | 128/287 |
| 3,586,593 | 6/1971 | Dahl | 156/522 X |
| 3,634,170 | 1/1972 | Hottendorf | 156/504 |
| 3,636,952 | 1/1972 | George | 128/287 |
| 3,661,680 | 5/1972 | Gore | 156/522 X |
| 3,666,611 | 5/1972 | Joa | 128/296 X |
| 3,673,019 | 6/1972 | Erekson | 156/552 X |
| 3,676,269 | 7/1972 | Schaetti | 156/291 X |
| 3,783,584 | 1/1974 | Rauser | 53/61 X |

*Primary Examiner*—David A. Simmons
*Attorney, Agent, or Firm*—Bell, Seltzer, Park & Gibson

[57] ABSTRACT

An apparatus and method for successively forming disposable diapers wherein the diaper includes a fluid-permeable top cover layer, a moisture-absorbent core under the top cover layer and including a pad of fibrous material and sheets of cellulosic material on each side of the pad, and a fluid-impervious bottom cover layer under the interior core and secured to the top cover layer along longitudinal and transverse edges thereon. The apparatus and method include mechanisms for and steps of, as follows. Supplying and positioning an elongate moisture-absorbent core including a pad of fibrous material of less width than the width of the core and sheets of cellulosic material on each side of the pad. Embossing and securing the sheets of cellulosic material together along longitudinally-extending areas on each side of the pad for forming an envelope of the sheets of cellulosic sheets around the pad. Supplying and positioning an elongate fluid-permeable top cover layer on the top of the core and an elongate fluid-impervious bottom cover layer under the core. Feeding the superimposed top cover layer, interior core and bottom cover layer along a predetermined longitudinal path of travel. Applying a plurality of short, spaced-apart, generally longitudinally-extending, adhesive strips between the top cover layer and the bottom cover layer transversely across the superimposed top cover layer and bottom cover layer at longitudinally-spaced intervals for transversely securing the top cover layer and the bottom cover layer together at longitudinally-spaced intervals to form successively interconnected diapers. Securing the top cover layer and the bottom cover layer together along longitudinal side edges of the successively interconnected diaper. Transversely severing the successively interconnected diapers generally medially of the plurality of the longitudinally-extending adhesive strips to form individual diapers.

24 Claims, 26 Drawing Figures

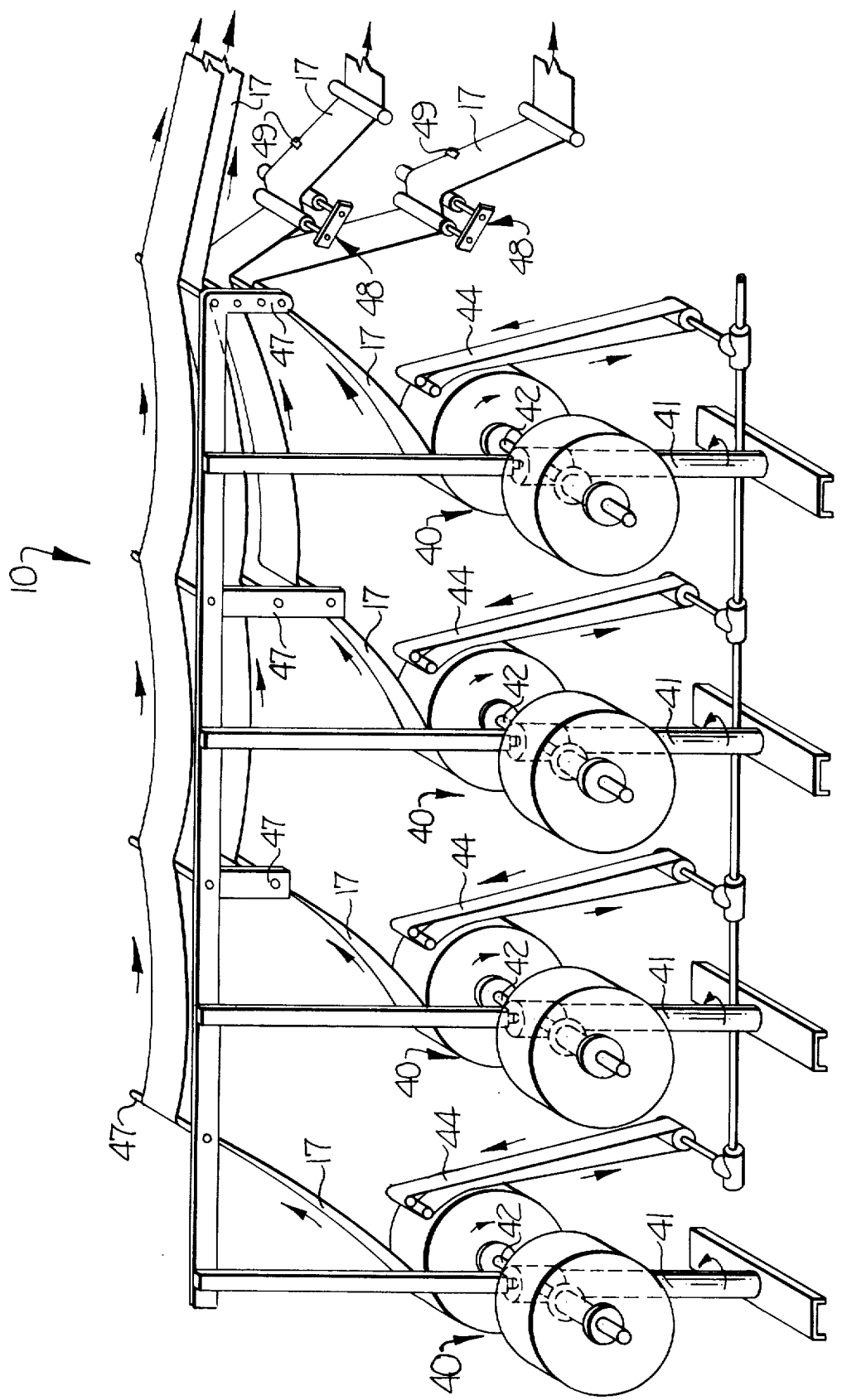

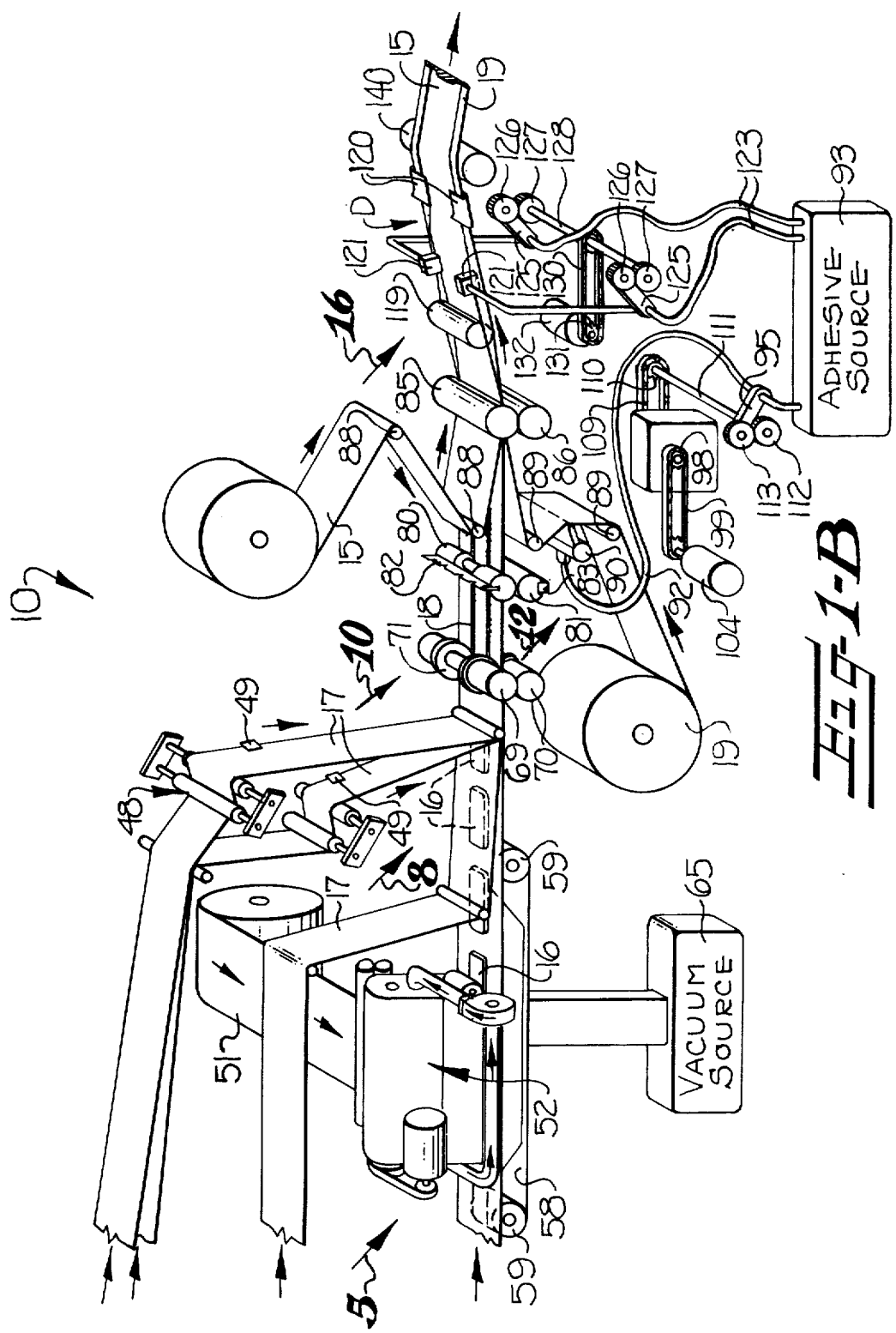
FIG-1-B

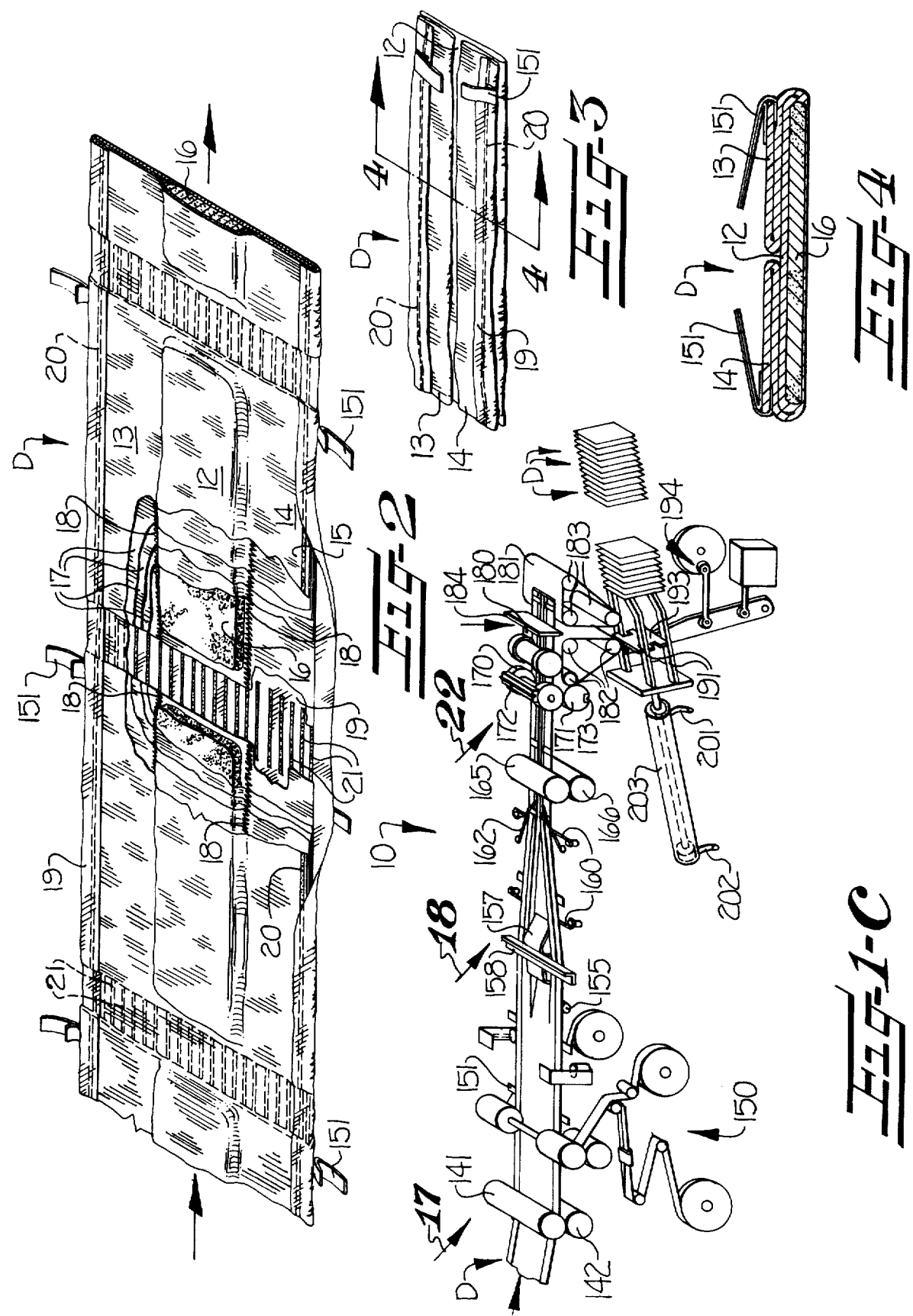

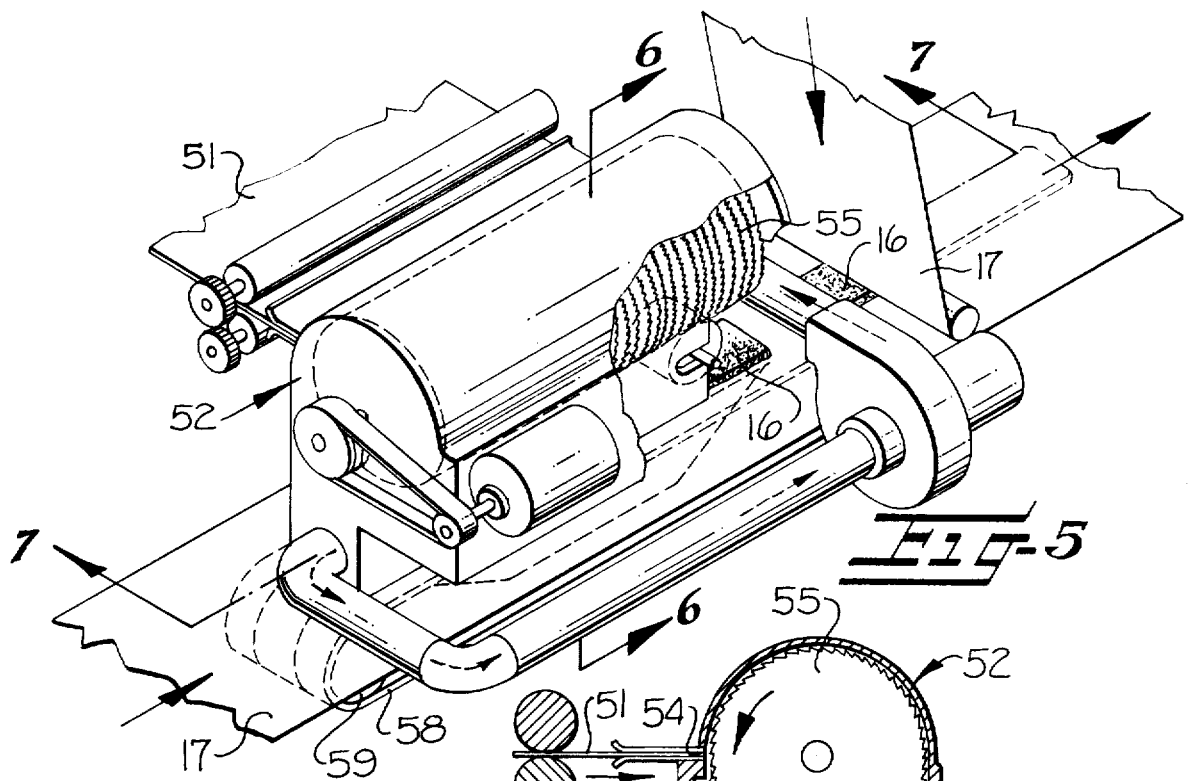
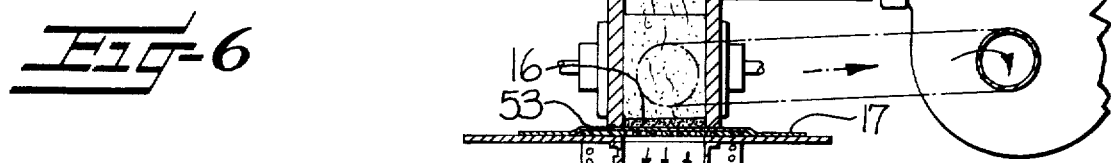
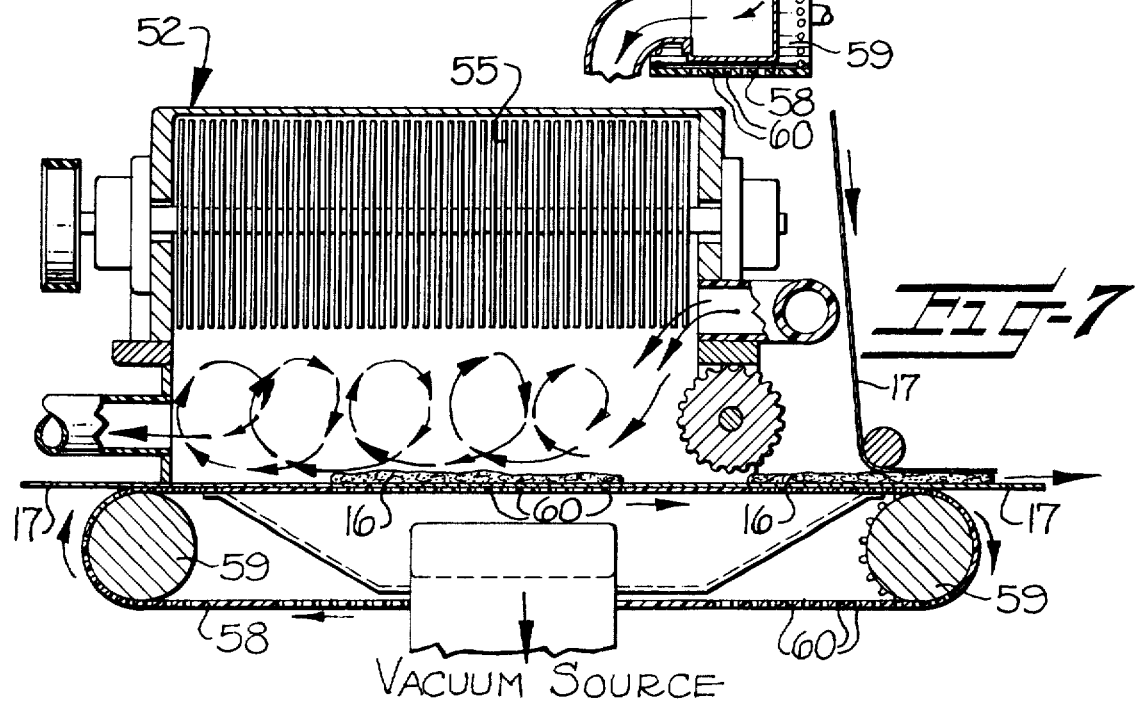

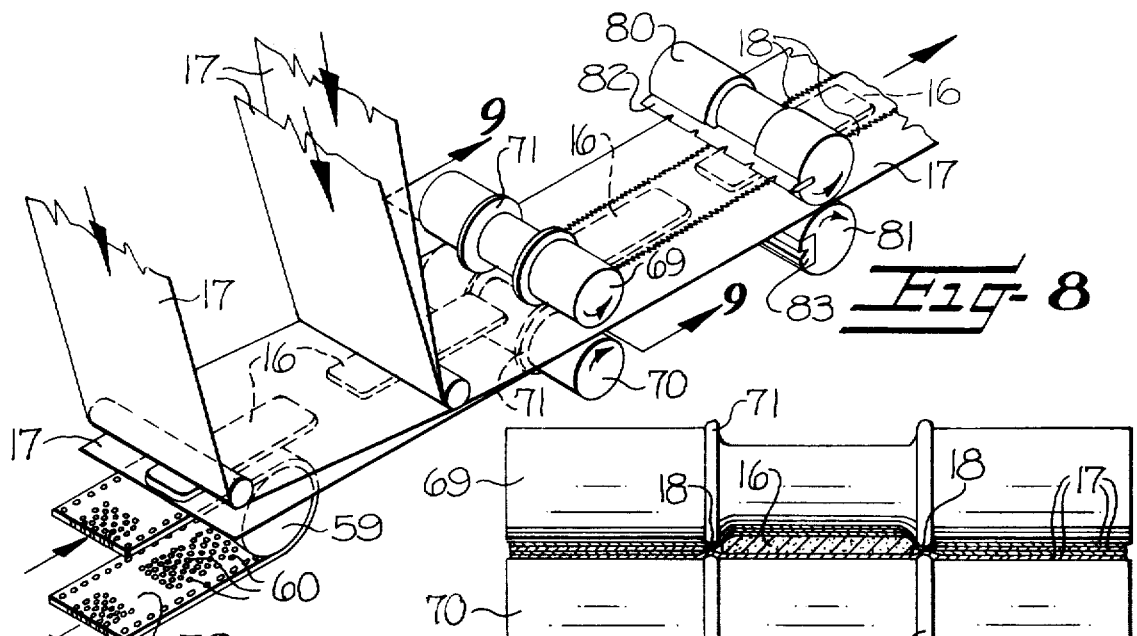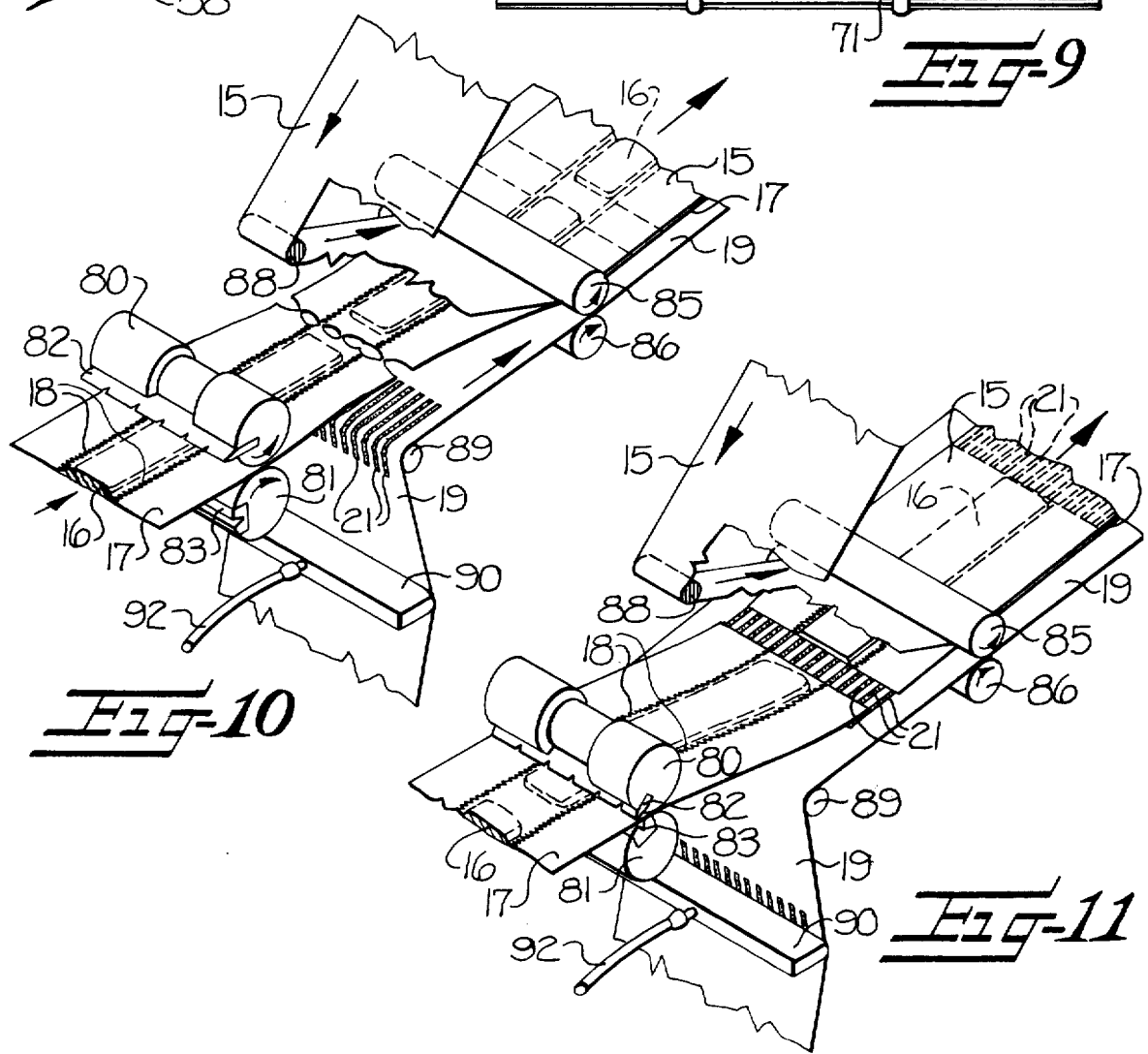

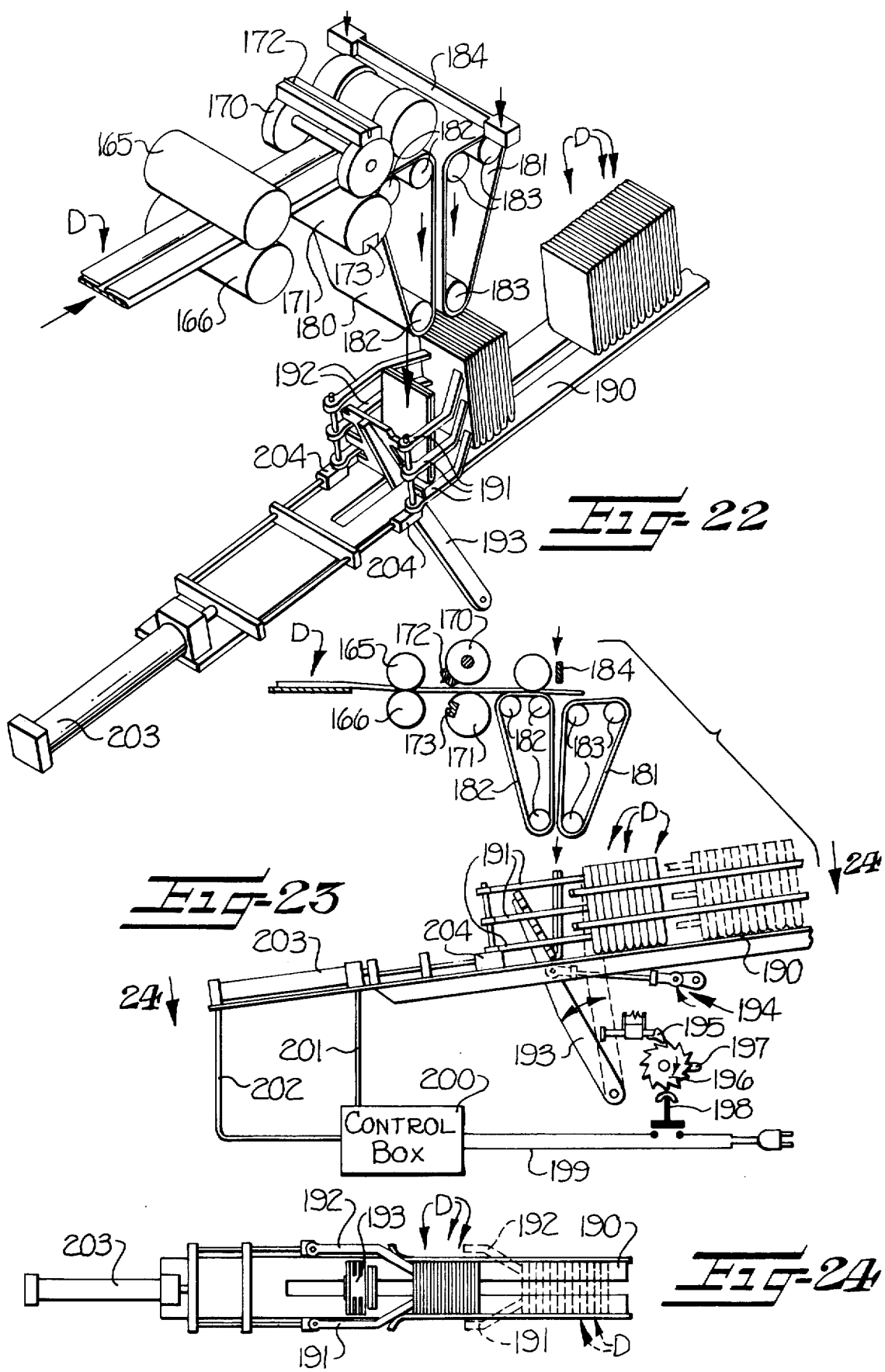

METHOD AND APPARATUS FOR SUCCESSIVELY FORMING DISPOSABLE DIAPERS

BACKGROUND OF INVENTION

This invention relates to an apparatus and method for successively forming disposable diapers wherein each diaper includes a fluid-permeable, top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon.

More particularly, the preferred method and apparatus of this invention relates to successively forming the prefolded disposable diapers disclosed in U.S. patent application Ser. No. 460,916, filed Apr. 15, 1974, and assigned to the assignee of the present invention.

Although methods and apparatuses have been previously proposed for successively fabricating disposable diapers, these methods and apparatuses do not lend themselves to automatically and successively forming disposable diapers of the above-described constructions and are for the most part complicated, intricate and expensive in design. In this regard, the assignee of the present invention has successfully developed and commercially utilized an apparatus for successively forming disposable diapers, as disclosed in U.S. Pat. No. 3,661,680, issued May 9, 1972 reissued as U.S. Pat. RE No. 28,139 on Aug. 27, 1974, and assigned to the assignee of the present invention. However, the present invention improves and includes additional desirable features over the previously patented apparatus.

SUMMARY OF INVENTION

Accordingly, it is the object of this invention to provide an improved apparatus and method for successively forming disposable diapers and, more specifically, such an improved method and apparatus for forming disposable diapers including a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon.

It has been found by this invention that the above objects may be accomplished by providing a method and apparatus including combinations of the following steps and mechanisms.

Means are provided for supplying and positioning an elongate moisture-absorbent core including a pad of fibrous material of less width than the width of the core and sheets of cellulosic material on each side of the pad. Means are provided for embossing and securing the sheets of cellulosic material together along longitudinally-extending areas on each side of the pad for forming an envelope of the sheets of cellulosic material around the pad. Means cooperate with the core supplying and positioning means for supplying and positioning an elongate fluid-permeable top cover layer in superimposed relation on top of the core. Means also cooperate with the core supplying and positioning means for supplying and positioning an elongate fluid-impervious bottom cover layer under the core. Means cooperate with the core, top cover layer and bottom cover layer supplying and positioning means for receiving and feeding the superimposed top cover layer, interior core and bottom cover layer along a predetermined longitudinal path of travel. Means cooperate with the supplying and positioning means and the receiving and feeding means for applying a plurality of short, spaced-apart, generally longitudinally-extending, adhesive strips between the top cover layer and the bottom cover layer transversely across the superimposed top cover layer and bottom cover layer at longitudinally-spaced intervals for transversely securing the top cover layer and the bottom cover layer together at longitudinally-spaced intervals to form successively interconnected diapers. Means cooperate with the receiving and feeding means for securing the top cover layer and the bottom cover layer together along longitudinal side edges of the successively interconnected diapers. Means cooperate with the receiving and feeding means for transversely severing the successively interconnected diapers generally medially of the plurality of longitudinally-extending strips to form individual diapers.

Preferably, the means for supplying and positioning the elongate moisture-absorbent core include means for fiberizing a sheet of wet-pressed, pulp fibers into individual fibers and forming individual, longitudinally spaced-apart pads of such fibers onto the continuous sheet of cellulosic material positioned under the pad.

It is also preferable for the method and apparatus of this invention to include cutting means cooperating with the positioning means for partially cutting the elongate core transversely thereof between the spaced-apart pads of fibers prior to the positioning of the top and bottom cover layers by the supplying and positioning means, and drafting means cooperating with the top and bottom cover layer positioning means and the receiving and feeding means for drafting the partially cut elongate core to separate the elongate core into longitudinally spaced-apart individual cores as the top and bottom cover layers are positioned on each side thereof by the supplying and positioning means. The means for applying the plurality of adhesive strips cooperates with the drafting means to position the adhesive strips between the bottom cover layer and the top cover layer at the spacing between the individually formed core members.

It is preferable for the bottom cover layer to be wider than the diaper being formed so that the bottom cover layer includes outer longitudinal edge portions extending outwardly from each side of the successively interconnected diapers when the bottom cover layer is positioned under the core and for the means for securing the top cover layer and the bottom cover layer together at the longitudinal side edges to comprise adhesive applying means cooperating with the receiving and feeding means for applying continuous longitudinally-extending lines of adhesive onto the top cover layer adjacent the outer longitudinal edges of the successively interconnected diaper, and folding means for folding the outer extending longitudinal edge portions of the bottom cover layer over the top of the top cover layer and over the longitudinally-extending adhesive lines for securing the folded over portions of the bottom cover layer to the top cover layer.

It is preferable to include means cooperating with the receiving and feeding means for longitudinally folding the successively interconnected diapers along longitudinally-extending fold lines so that the side portions of the successively interconnected diapers are folded inwardly over the central portion of the successively interconnected diapers and then folded outwardly back over themselves to form prefolded successively interconnected diapers.

The apparatus and method may also preferably include means cooperating with the receiving and feeding means for applying a pair of elongate securing tabs having adhesive on one face thereof to the outer longitudinal edges, respectively, of the bottom cover layer, and means cooperating with the receiving and feeding means and positioned subsequent to the transverse severing means for successively receiving the individual diapers and counting a predetermined number of such diapers and separating the predetermined number of such diapers for packaging.

BRIEF DESCRIPTION OF THE DRAWINGS

Some of the objects and advantages of this invention having been stated, other objects and advantages will appear as the description proceeds, when taken in conjunction with the accompanying drawings, in which:

FIGS. 1-A, 1-B and 1-C are schematic, perspective views of successive portions of the preferred apparatus of the present invention for forming prefolded disposable diapers;

FIG. 2 is a partial, perspective view, partially broken away, of the successively interconnected diapers formed by the apparatus of this invention prior to being folded and transversely cut for separating into individual diapers;

FIG. 3 is a perspective view of the preferred prefolded individual disposable diaper formed in accordance with the method and apparatus of this invention;

FIG. 4 is a schematic, cross-sectional view, taken generally along the line 4—4, of the diaper of FIG. 3;

FIG. 5 is an enlarged, perspective detail, partially broken away, of a portion of the apparatus of FIG. 1-B and taken generally at the arrow 5 of FIG. 1-B;

FIG. 6 is a cross-sectional view, taken generally along the line 6—6 of FIG. 5;

FIG. 7 is a cross-sectional view, taken generally along the line 7—7 of FIG. 5;

FIG. 8 is an enlarged, perspective detail of a portion of the apparatus of FIG. 1-B and taken generally at the arrow 8 of FIG. 1-B;

FIG. 9 is a cross-sectional view, taken generally along the line 9—9 of FIG. 8;

FIGS. 10 and 11 are enlarged, perspective details of a portion of the apparatus of FIG. 1-B and taken generally at the arrow 10 of FIG. 1-B and illustrating successive conditions of the diaper component materials being fed therethrough;

FIG. 22 is an enlarged, perspective detail of a portion of the apparatus shown in FIG. 1-C and taken generally at the arrow 22 of FIG. 1-C;

FIG. 23 is a schematic, side elevational view generally of the apparatus of FIG. 22; and FIG. 24 is a view taken generally along the line 24—24 of FIG. 23.

DESCRIPTION OF PREFERRED EMBODIMENT

Figure 12:
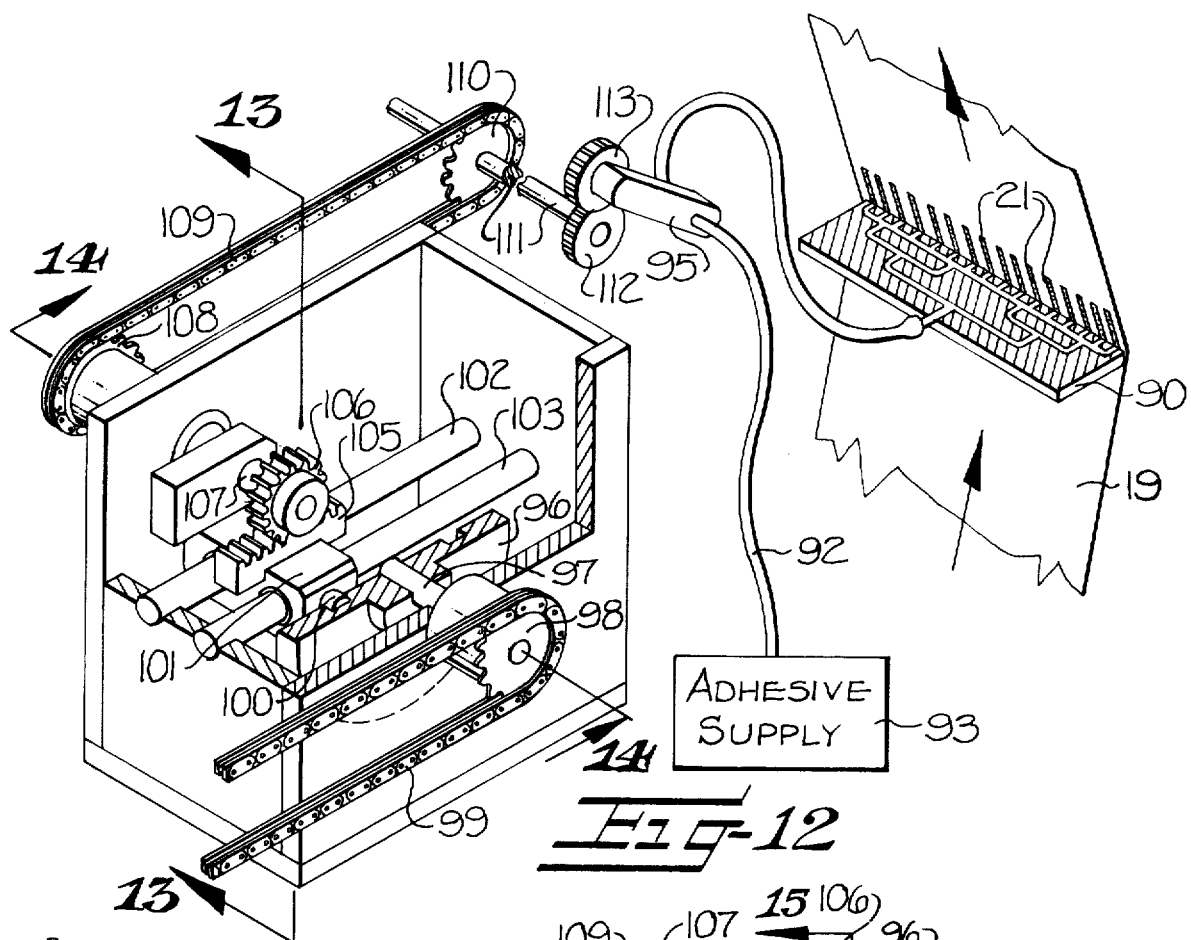
FIG. 12 is an enlarged, perspective detail, partially broken away, of a portion of the apparatus of FIG. 1-B and taken generally at the arrow 12 of FIG. 1-B.
Figure 13:
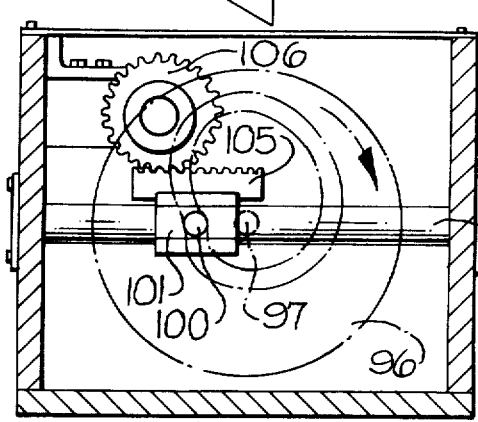
FIG. 13 is a cross-sectional view, taken substantially along the line 13—13 of FIG. 12.
Figure 14:
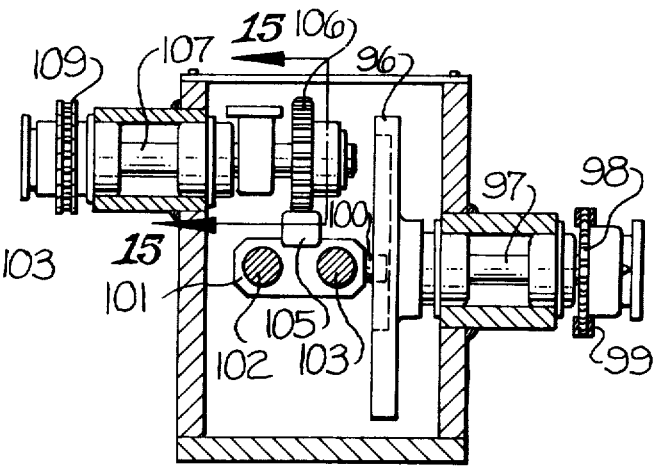
FIG. 14 is a cross-sectional view, taken substantially along the line 14—14 of FIG. 12.
Figure 15:
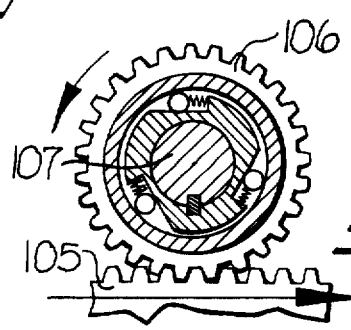
FIG. 15 is an enlarged, cross-sectional detail, taken generally along the line 15—15 of FIG. 14.
Figure 16:
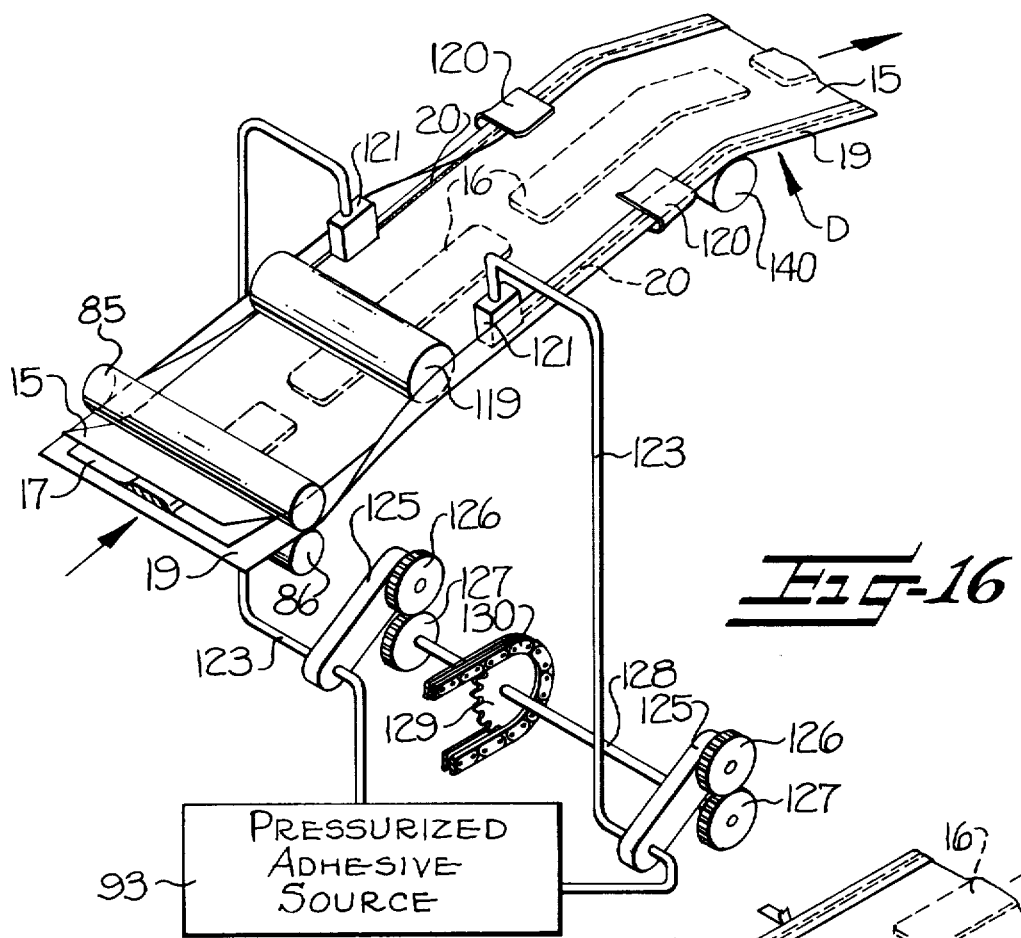
FIG. 16 is an enlarged, perspective detail of a portion of the apparatus shown in FIG. 1-B and taken generally at the arrow 16 of FIG. 1-B.
Figure 17:
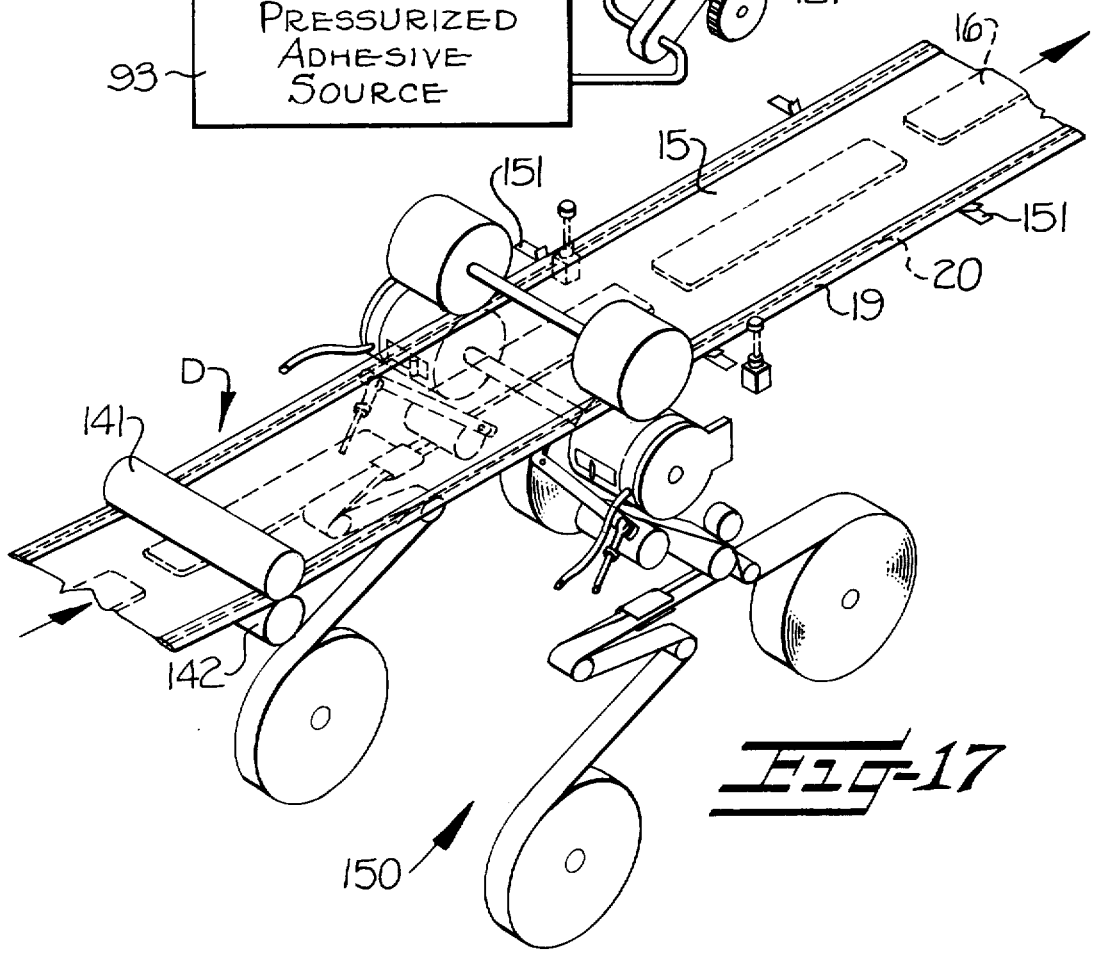
FIG. 17 is an enlarged, perspective detail of a portion of the apparatus shown in FIG. 1-C and taken generally at the arrow 17 of FIG. 1-C.
Figure 18:
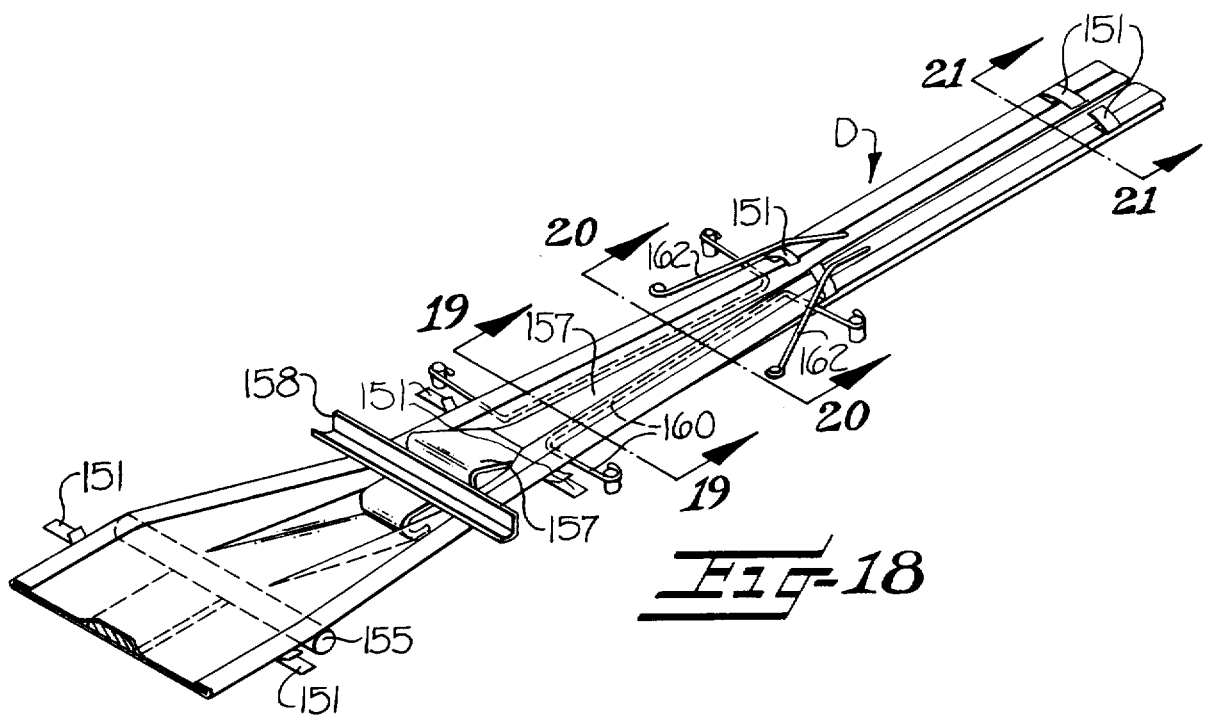
FIG. 18 is an enlarged perspective detail of a portion of the apparatus shown in FIG. 1-C and taken generally at the arrow 18 in FIG. 1-C.
Figure 19:
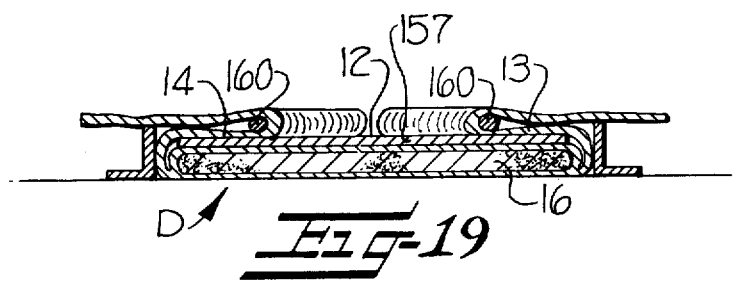
FIG. 19 is an enlarged cross-sectional view, taken generally along the line 19—19 of FIG. 18.
Figure 20:
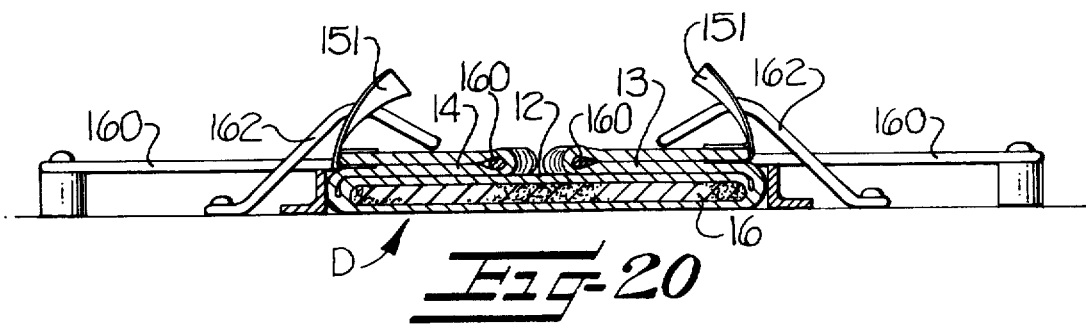
FIG. 20 is an enlarged, cross-sectional view, taken generally along the line 20—20 of FIG. 18.
Figure 21:
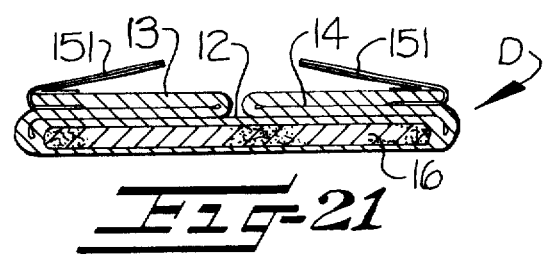
FIG. 21 is an enlarged, cross-sectional view, taken generally along the line 21—21 of FIG. 18.

Referring now to the drawings, FIGS. 1-A, 1-B and 1-C illustrates schematically the preferred embodiment of the apparatus, generally indicated at 10, for operating in accordance with the preferred method of the present invention for forming the preferred prefolded disposable diapers, generally designated by the reference numeral D and more fully illustrated in FIGS. 2–4. In the illustration of the apparatus 10 in FIGS. 1-A, 1-B and 1-C, the various drive for the various component mechanisms and the machine frames for supporting these mechanisms have been omitted for clarity and a better understanding of the component mechanisms of this invention. These various drives and frame portions do not constitute a part of the present invention and are not considered necessary for an understanding thereof. Any suitable drives and frames may be utilized with the illustrated mechanisms of the apparatus 10.

As discussed generally above and as may be seen in FIGS. 2–4, the preferred diaper construction D produced in accordance with the preferred apparatus 10 and method of the present invention comprises a generally rectangular unfolded configuration defining longitudinally extending central portion 12 and side portions 13, 14. In the prefolded condition, as shown in FIGS. 3 and 4, the side portions 13 and 14 are folded inwardly over the central portion 12 and then folded back over themselves to form a prefolded diaper D which may be easily fitted to the wearer.

The diaper D generally comprises a fluid-permeable, top cover layer of sheet material 15 for being placed in contact with the body of the wearer and for receiving the moisture of the wearer. The top cover layer 15 has generally the dimensions of the unfolded diaper and may be creped in the transverse direction of the diaper for wicking moisture toward the longitudinal edges of the unfolded diaper to prevent excess wicking of moisture toward the transverse edges of the diaper D. A moisture-absorbing interior core is positioned under the top cover layer 15 for absorbing the moisture of the wearer received therethrough and includes a pad of fiberized fibers 16 for providing superior moisture-absorbing characteristics. The interior pad 16 preferably has a width less than the width of the unfolded diaper D (see FIG. 2) and is disposed in the central portion 12 of the diaper only for concentrating absorbency therein and allowing easy folding of the diaper and has a longitudinal length less than the longitudinal length of the diaper so that the transverse edges of the interior pad 16 terminates short of the transverse edges of the diaper for reducing the bulk of the diaper at the edges thereof to aid in securing the various components of the diaper together and provide unbulky edges for a better fit on the wearer.

The interior core further includes sheets of cellulosic material 17 including one sheet positioned below the interior pad 16 and a plurality of sheets positioned on top of the interior pad 16 under the top cover sheet 15 for forming an interior envelope around the interior pad 16 to provide strength to and stabilize the interior pad 16 and provide additional absorbency to the diaper D. These interior sheets 17 have a width substantially the same as the unfolded diaper for providing absorbency throughout the width of the diaper and have a length less than the length of the diaper so that the transverse outer edges of the interior sheets terminate short of the transverse edges of the unfolded diaper D to aid in securing the various components of the diaper together.

The diaper D further includes longitudinally-extending embossed areas 18 securing the interior sheets 17 together on each side of the longitudinal edges of the interior pad 16 for retaining the interior pad in position in the central portion of the unfolded diaper D and to prevent transverse shifting of the interior pad 16 within the diaper D.

A protective, fluid-impervious, bottom, cover layer of sheet material 19 is positioned under the interior core to form with the top cover layer 15 an envelope around the interior core and for preventing moisture absorbed therein from passing out of the diaper. The bottom cover layer 19 has a longitudinal length the same as the unfolded diaper D and has a transverse width greater than the width of the unfolded diaper D and extends around the longitudinal edges of the unfolded diaper D and overlaps the top cover layer 15 for preventing leakage of moisture at the longitudinal edges of the unfolded diaper D.

A longitudinally-extending line of adhesive 20 along each longitudinal edge of the diaper D positioned between the top cover layer 15 and the overlapping portion of the bottom cover layer 19 secures these layers together along the longitudinal edges of the unfolded diaper D.

A plurality of short, spaced-apart, generally longitudinally-extending, adhesive strips 21 extend from each outer longitudinal edge of the unfolded diaper D inwardly between the top cover layer 15 and the bottom cover layer 19 and terminate slightly inside the interior sheets 17 for securing the top cover layer 15 and the bottom cover layer 19 together and for securing the interior sheets 17 thereto along the transverse edges of the unfolded diaper D. These transverse securements provide soft, flexible, transverse edges to the diaper for comfort when placed in position on the wearer.

While the overall preferred apparatus 10 of the present invention is specifically constructed and the preferred method of the present invention is specifically intended for constructing the above-described preferred diaper construction D, it will be apparent that other diapers or the like may be formed with the apparatus 10 and the method of this invention by making changes that will be apparent to one skilled in the art or by utilizing certain sub-combinations of the components of the apparatus 10 and the method of this invention.

Referring now to the apparatus 10, as illustrated in the drawings and first with reference to FIG. 1-A, means are provided for supplying and positioning the elongate moisture absorbent core including the pad 16 of fiberized material and the sheets 17 of cellulosic material positioned on each side of the pad. This means includes separate supply creels 40 for containing separate rolls of continuous cellulosic sheet material 17 and for supplying the sheets of cellulosic material 17 to the diaper forming apparatus 10. These supply creels 40 include a rotatably-mounted, vertically-extending, standard 41 which includes roll carrying shafts 42 extending horizontally outwardly from each side thereof for receiving a roll of sheet material 17 on each end thereof so that one roll of sheet material 17 may be positioned in a supply position and the other roll of sheet material 17 in a reserve position. When the roll of sheet material in the supply position has been exhausted, the rotatable standard 41 may be rotated to place the reserve roll in the supply position and the exhausted roll, now in the reserve position, may be replaced. The rolls of sheet material 17 in the supply position are contacted by surface drive conveyor belt units 44 for rotating each of the rolls of sheet material 17 in the supply position in synchronism for supplying the sheet material 17 to the apparatus 10.

The continuous sheets of material 17 pass from the supply rolls thereof through suitable guide units, collectively indicated at 47, and are received by identical aligning means, generally indicated at 48, which align the sheets 17 directly above each other for thereafter being fed into superimposed relation. These edge aligning devices 48 are of conventional, commercially available, construction and, accordingly, will not be described in detail. It suffices to say that each of the sheets 17, passes between a pair of cooperating rolls in each aligning device 48 which rolls are laterally shiftable in response to an edge sensing of the respective positions of the sheet 17 by a sensing head 49 which causes the aligning mechanisms 48 to be shifted to maintain the respective sheets 17 in alignment with each other and advancing along a predetermined path of travel.

Simultaneously with the feeding of the sheets of cellulosic material 17, individual, spaced-apart pads 16 of fibers are being formed as part of the interior core with the sheets 17. For this purpose, a generally enclosed, stationary, fiberizing and pad forming chamber mechanism 52 (see FIGS. 1-B and 5-7) is provided. This chamber mechanism 52 has an open bottom 53 and a slot 54 in an upper portion thereof to receive a continuous sheet 51 of wet-pressed pulp fibers. A rotatably mounted and driven fiberizing device 55 is mounted in the upper portion of the chamber mechanism 52 for contacting the sheet 51 of wet-pressed pulp fibers and fiberizing the sheet into substantially individual fibers.

A driven, longitudinally moving endless conveyor belt 58 is carried by a pair of driven rolls 59 for receiving on the top surface thereof the sheet of cellulosic material 17 to be positioned under the pads 16 forming part of the interior core of the diaper D. The conveyor belt 58 is moving in the direction of the arrows shown in FIGS. 5 and 7 and includes longitudinally-spaced groups of small perforations 60 (see FIGS. 7 and 8) therein along the length thereof corresponding to the desired configuration and spacing of the fiber pads 16 being formed. The conveyor belt 58 is positioned for movement along the open bottom end 53 of the chamber mechanism 52 directly below the fiberizing device 55 and cooperates with the chamber mechanism 52 for ming an enclosed pad forming area in a lower portion of the chamber mechanism 52. As the conveyor t 58 and the sheet 17 of cellulosic material carried thereby passes through the pad forming area in the lower portion of the chamber mechanism 52, the fiberized fibers are received on the upper surface thereof of the sheet 17 and the fiberized fibers are conveyed out of the chamber mechanism 52.

A stationary vacuum device 65 is positioned at the lower surface of the conveyor belt 58 and directly below the chamber mechanism 52 and is connected with any suitable source of vacuum for creating a vacuum through the groups of perforations 60 in the conveyor belt 58 and through the sheet of cellulosic material 17 being carried thereon for causing the fiberized fibers to be pulled through the groups of perforations 60 to form individual, longitudinally spaced-apart pads 16 on the sheet of cellulosic material 17 and on the moving conveyor belt 58 over the groups of perforations 60 and within the lower portion of the chamber mechanism 52 for being conveyed by the conveyor belt 58 out of the chamber mechanism 52 after formation thereof.

Thus, longitudinally spaced-apart pads 16 of fiberized fibers are formed onto the continuous sheet of cellulosic material 17. The above-described fiberizing and pad forming apparatus is the subject of U.S. patent application Ser. No. 415,010, filed Nov. 12, 1973, now U.S. Pat. No. 3,857,657, issued Dec. 31, 1974 and assigned to the assignee of the present invention, and reference may be had thereto for further details of the construction and operation of such fiberizing and pad forming mechanism.

As the spaced-apart, individual pads 16 and the sheet of cellulosic material 17 positioned thereunder are fed away from the fiberizing and pad forming chamber mechanism 52, another sheet of cellulosic material 17 is positioned on top of the spaced apart pads 16, as shown in FIG. 1-B. Thereafter, additional sheets of cellulosic material 17 are positioned on top of the pads 16.

The thus formed elongate continuous interior core is fed through a means for embossing and securing the sheets of cellulosic material 17 along the longitudinal-extending areas 18 on each side of the spaced-apart pads 16 for forming an envelope of the sheets of cellulosic material 17 around the spaced-apart pads 16. This means comprises a pair of driven, rotating, cooperating rolls 69, 70 positioned generally transversely of the elongate interior core on each side thereof so that the interior core passes therebetween. As seen particularly in FIGS. 8 and 9, these rotating rolls 69, 70 include embossing collars 71 extending around the circumference thereof and outwardly therefrom for engagement with each other for pressing and embossing the sheets of cellulosic material 17 together at the areas 18 on each side of the interior pads 16. The top roll 70 includes a suitable cut out portion between the embossing collars 71 for passage of the thickened interior pad 16.

After the above-described embossing operation, the thus formed elongate continuous interior core is fed through cutting means (see FIGS. 1-B, 10 and 11) for partially cutting the elongate core transversely thereof between the spaced-apart interior pads 16 forming part of the interior core. This cutting means is in the form of a pair of transversely extending, driven, rotating feed rolls 80, 81 positioned on each side of the elongate continuous core for forming a nip therebetween for receiving and feeding therethrough the elongate continuous core. The roll 80 includes a serrated knife member 82 extending outwardly therefrom along the length thereof and the roll 81 includes an indented anvil member 83 extending along the length thereof for receiving the blade 82 and acting as an anvil for partially cutting the elongate continuous core transversely thereof when the blade 82 and the anvil member 83 are rotated into engagement with each other. The size of the rolls 80, 81, the spacing of the knife member 82 and anvil member 83 and the speed of rotation is coordinated with the distance between the spaced-apart pads 16 so that the partial or serrated cut will be positioned between the spaced-apart pads 16 (see FIG. 10). Thus, the continuous elongate core will be partially cut transversely across its width after passing between the rolls 80, 81.

Cooperating with the above-described partial cutting means is a drafting means for drafting the partially cut elongate, continuous, interior core to pull the core apart at the location of the partial cut placed therein to separate the elongate continuous core into longitudinally spaced-apart individual cores. This drafting means comprises a pair of driven, rotating rolls 85, 86 which extend transversely across the core and are positioned on each side of the core for forming a nip for receiving and passing the core therethrough. The speed of rotation of the rolls 85, 86 is coordinated with the speed of rotation of the rolls 80, 81 so that the rolls 85, 86 are slightly overfed to draft the elongate continuous core in the area between the rolls 80, 81 and 85, 86 so as to pull the core apart at the location of the serrated or partial cut to separate the continuous core and form individual, spaced-apart cores, as shown in FIG. 11.

Cooperating with the above-described mechanisms is a means for supplying and positioning the elongate fluid-permeable top cover layer 15 on top of the spaced-apart individual cores 16. This means comprises a supply roll of top cover layer material 15 which is suitably mounted by any convenient mechanism for supplying the sheet material 15 around suitably positioned guide rolls 88 to be received over the spaced-apart individual cores and between the driven rolls 85, 86, as shown in FIG. 1-B.

Similarly cooperating with the above-described mechanisms is a means for supplying and positioning the elongate fluid-impervious bottom cover layer 19 under the individual spaced-apart cores 16. This means comprises a supply roll of bottom cover layer material 19 which is suitably mounted by any convenient mechanism for supplying the sheet material 19 around suitably positioned guide rolls 89 to be received under the spaced-apart individual cores 16 and between the driven rolls 85, 86 as shown in FIG. 1-B.

Cooperating with the above-described supplying and positioning means is means for applying the plurality of short, spaced-apart, generally longitudinally-extending, adhesive strips 21 between the top cover layer 15 and the bottom cover layer 19 transversely across the superimposed top cover layer and bottom cover layer at longitudinally-spaced intervals between the individual spaced-apart cores for transversely securing the top cover layer 15 and the bottom cover layer 19 together to form successively interconnected diapers D.

This means comprises generally an adhesive strip extruding head 90 (see FIGS. 1-B, 10, 11 and 12–15) positioned adjacent the top face of the bottom cover layer 19 in its path of travel as it is being supplied and positioned by the bottom cover layer supplying and positioning means prior to being positioned under the core and as the bottom cover layer 19 passes between drive roll 89 for extruding the plurality of short, spaced-apart, generally longitudinally-extending, adhesive strips 21 onto the top face of the bottom cover layer 19. The adhesive strips extruding head 90, as shown in FIG. 12, includes channels extending therethrough and terminating in apertures or nozzles which engage the top face of the bottom cover layer 19 for extruding the adhesive strips 21 thereon.

Connected with the extruding head 90 is an adhesive conveying conduit 92 which is connected at one end with the extruding head 90 and at the other end with any suitable adhesive supply 93, shown only schematically in the drawings, for supplying adhesive to the extruding head 90. Positioned in the adhesive conduit 92 is a pump 95 for being intermittently operated for intermittently pumping and supplying adhesive to the extruding head 90 for intermittently extruding short adhesive strips 21 onto the top face of the bottom cover layer 19.

For intermittently driving the pump 95 there is provided a drive mechanism including a rotatably mounted cam 96 carried on the end of a shaft 97 extending from a sprocket 98 driven by a chain 99. The chain 99 may be driven by a suitable motor 104. The cams 96 receive a follower 100 which is secured to the end of a slide 101 mounted on a pair of stub shafts 102, 103. The slide 101 moves linearly along the stub shafts 102, 103 under the action of the cam follower 100 in the profile of the cam 96. The slide 101 includes a gear 105 which engages a sprocket gear 106 mounted on the end of a stub shaft 107 which carries a sprocket gear 108 on the other end thereof. The sprocket gear 108 receives an endless drive chain 109 which also passes around a sprocket 110 which is carried on a stub shaft 111. The stub shaft 111 includes a gear 112 on the other end thereof which is in meshing engagement with a gear 113 on the pump 95 for driving the pump.

Thus, it may be seen that rotation of the cam 96 will cause linear movement of the slide 101 through reception of the follower 100 in the profile of the cam 96 which in turn will cause intermittent rotation of the gear 106 and thus intermittent driving of the pump 95 through the above-described mechanical connections. The profile of the cam 96 is arranged such that the pump 95 will be intermittently driven for extruding adhesive strips 21 onto the top face of the bottom cover layer 19 at locations which will position these strips between the spaced-apart individual interior cores when the bottom cover layer 19 is positioned under the spaced-apart cores and the top cover layer 15.

The above-described intermittently operated glue extruding apparatus is the subject of U.S. patent application, being filed concurrently herewith, Ser. No. 491,765, filed July 25, 1974 and assigned to the assignee of the present invention, and further details with respect to the operation and construction thereof may be had by reference to that patent application.

The thus formed continuous length of successively interconnected diapers D including the top cover layer, interior core and bottom cover layer are then fed past a driven, rotating roll 119 which presses the above-described components of the successively interconnected diapers D together. The successively interconnected diapers are then passed through a means for securing the top cover layer 15 and the bottom cover layer 19 together along the longitudinal side edges thereof. As discussed above, the bottom cover layer 19 has a transverse width greater than the width of the unfolded diapers D and the continuous length of successively interconnected diapers D so that the bottom cover layer 19 may be folded around the longitudinal edges of the successively interconnected diapers and overlap the top cover layer 15. For this purpose, the outer longitudinal edges of the bottom cover layer 19 comes into contact with generally U-shaped folding blades 120 positioned on each side of the successively interconnected diapers D as they travel in advance of the roll 119 for engaging the extending sides of the bottom cover layer 19 and folding these extending sides around the longitudinal edges of the successively interconnected diapers and over the top of the top cover layer 15.

Just prior to engagement with the folding blades 120 in the path of travel of the successively interconnected diapers, there is provided adhesive extruding heads 121 positioned on each longitudinal edge of the successively interconnected diapers D for applying the continuous longitudinally-extending lines of adhesive 20 onto the top cover layer 15 adjacent each outer longitudinal edge of the successively interconnected diapers so that when the successively interconnected diapers engage the folding blades 120, the overlapping bottom cover layer 19 will be pressed into engagement with the continuous lines of adhesive 20 for securing the bottom cover layer to the top cover layer and provide securements at the longitudinal edges of the successively interconnected diapers D.

Adhesive material is supplied to the extruding heads 121 from any convenient pressurized adhesive source (shown schematically in FIGS. 1-B and 16) through conduits 123 to each of the extruding heads 121. Positioned in each of the conduits 123 is a pump 125 for being driven to pump the adhesive from the source through the conduit 123 to the extruding heads 121. These pumps 125 may be conveniently driven by a sprocket gear 126 extending from each of the pumps 125 and engaging a sprocket gear 127 on each end of a shaft 128. The shaft 128 includes a gear 129 which is driven by a chain 130 which also passes around a gear 131 from a motor 132.

From the above-described longitudinal edge securing means, the successively interconnected diapers D, now secured along their longitudinal edges, pass over a roll 140 which aids in pressing the components of the successively interconnected diapers D together. From the roll 140, the successively interconnected diapers D which have been secured along their longitudinal edges pass through a pair of driven rolls 141, 142 which form a nip therebetween for the passage therethrough of the successively interconnected diapers. From the rolls 141, 142, the successively interconnected diapers pass through a means 150 for applying a pair of elongate securing tabs 151 having adhesive and release paper on one face thereof to the outer longitudinal edges, respectively, of the bottom cover layer. This securing tab applying means 150 is the subject of United States patent application Ser. No. 385,832, filed Aug. 6, 1973, and assigned to the assignee of the present invention, and reference may be had thereto for full details of this mechanism and its operation. For an understanding of the present invention, suffice it to say that the mechanism 150 is intermittently applying elongate securing tabs 151 on each longitudinal edge of the successively interconnected diapers D so that a pair of securing tabs is disposed on each diaper D for use in securing the diaper in position on the wearer.

The successively interconnected diapers D then pass over a guide bar 155 and through means for longitudinally folding the successively interconnected diapers along longitudinally-extending fold lines so that the side portions 13, 14 of the successively interconnected diapers D are folded inwardly over the central portion 12 and then folded outwardly back over themselves to form prefolded successively interconnected diapers D, as shown in FIGS. 1-C and 18–21.

This folding means comprises a longitudinally-extending folding plate 157 carried by a transversely extending bar 158 for engaging the central portion of the successively interconnected diapers and holding this central portion against any folding action and allowing the folding over of the side portions 13, 14 of the successively interconnected diapers D around the edges thereof and over the central portion 12. For folding over the side portions 13, 14 of the successively interconnected diapers D, there is provided a first pair of longitudinally-extending, inwardly tapering folding bars 160 positioned generally above the folding plate 157 for engaging the side portions 13, 14 of the successively interconnected diapers D and causing these side portions 13, 14 to fold inwardly over the central portion 12 and around the folding plate 157 and then outwardly back over themselves to form the prefolded interconnected diapers D. This folding action may be clearly seen in FIGS. 18–21.

If desired, a pair of folding bars 162 may be positioned subsequent to the folding bars 160 for folding over the outwardly extending securing tabs 151 which have been applied to the successively interconnected diapers D. Also, cooperating with the above described folding plate 157 and folding bars 160 is a pair of transversely extending, driven, rotating rolls 165, 166 which form a nip therebetween for receiving the prefolded, successively interconnected diapers therebetween for pressing the successively interconnected diapers into their prefolded condition.

Next, there is provided a means for transversely severing the prefolded, successively interconnected diapers D generally medially of the transverse securements, which comprise the plurality of longitudinally-extending adhesive strips 21 to form individual diapers D. This means comprises a pair of driven rotating rolls 170, 171 positioned on opposite sides of the successively interconnected prefolded diapers and extending transversely thereof. The roll 170 carries a transversely extending knife member 172 and the roll 171 carries a transversely extending anvil member 173. As the rolls 170 and 171 are rotated in the direction of travel of the prefolded successively interconnected diapers D, the knife member 172 comes into engagement with the anvil member 173 at the transverse securements or adhesive strips 21 between the successively interconnected diapers D to cut the successively interconnected diapers D transversely thereof to separate and form individual diapers D. The size of the rolls 170, 171, the spacing of the knife member 172 and the anvil member 173 and the speed of rotation thereof is coordinated with the distance between the transverse securements of the successively interconnected diapers D so that the cut will be made generally medially of the adhesive strips 21.

These individually cut diapers D are then received onto the upper flight of a pair of conveyor belts 180, 181 which are being rotated in opposite directions by any convenient drive rolls 182, 183 so as to form a nip therebetween and force the individually cut diapers D therebetween, as shown particularly in FIGS. 1-C, 22 and 23. Cooperating with the oppositely rotating conveyor belts 180, 181 is a reciprocating blade 184 which is adapted to engage the individually cut diapers D generally medially thereof and force the middle portion of the individually cut diapers D into the nip between the oppositely rotating conveyor belts 180, 181 for folding the individually cut diapers D generally in half about a transversely extending fold line at generally the medial portion of the individual cut diapers D.

The thus folded individually cut diapers D are then carried down through the nip between the conveyor belts 180, 181 and are received by a means for counting a predetermined number of such individually cut and folded diapers D and separating the predetermined number of such diapers for packaging, as shown in FIGS. 1-C and 22–24. This counting mechanism is the subject of United States patent application, being filed concurrently herewith, Ser. No. 491,389 filed July 24, 1974, and assigned to the assignee of the present invention, and full details of the operation thereof may be had by reference to that application.

For purposes of understanding the present invention, this counting mechanism generally comprises a stationary slide 190 for receiving the generally vertically extending, individually cut and folded diapers D. This slide 190 may be supported by any suitable frame device of the apparatus 10 of this invention. The individual diapers D are received between pivotally mounted sets of finger mechanisms 191 and 192. These sets of finger mechanisms 191, 192 are spring biased by any suitable mechanism (not shown) toward the center of the slide device 190. After each individual diaper D is received between the sets of finger mechanisms 191, 192, a reciprocating pusher plate device 193 engages the diaper D and pushes it forwardly moving the finger devices 191, 192 outwardly against their bias for forcing the diaper D forwardly thereof. The reciprocating pusher plate mechanism 193 then reciprocates backwardly to its beginning position, shown in solid lines in FIGS. 22 and 23, and the diaper D is retained forwardly of the finger mechanisms 191, 192.

Any suitable crank arm device 194 may be utilized for reciprocating the pusher plate mechanism 193. During each reciprocation of the pusher plate mechanism 193, a pick member 195 is engaged and pushed forwardly. The forward end of the pick member 195 is in engagement with a toothed pick gear 196 which is caused to rotate by one tooth during each forward reciprocation of the pusher member 193 and the pick member 195. The pick gear 196 includes an outwardly extending wand 197 which, after rotation of the pick gear 196 a predetermined number of teeth corresponding to the predetermined number of diapers being counted, will engage a switch 198 connected in an electrical circuit 199 to a control mechanism 200 for controlling the flow of fluid under pressure through conduits 201 and 202 to each side of a fluid operated piston-cylinder device 203. The fluid operated piston-cylinder device 203 is connected at its forward end to a pusher mechanism 204 which will be operated by the piston-cylinder device 203, upon actuation of the switch 198 after a predetermined number of diapers has been counted, to come into engagement with the counted stack of diapers forwardly of the finger mechanisms 191, 192 to push this stack forwardly for removal by an operator of a predetermined number of diapers.

Referring now to the overall apparatus 10 of this invention, the rolls 69 and 70, 80 and 81, 85 and 86, 141 and 142, 165 and 166, and 170 and 171 may all be driven rolls which receive and feed the components of the diapers D in a generally linear, longitudinal path of travel through the various operating mechanisms of the machine 10 of this invention for fabricating diapers D. These rolls may all be driven in desired synchronism with each other for providing the above-described desired operations. Inasmuch as the drive mechanisms for these rolls do not constitute a part of the present invention, as stated above, and the construction of such an interconnected, synchronized drive is well within the skill of one with ordinary skill in the art, it is believed that the invention is more clearly presented and the drawings are less cluttered without an illustration and description of this interconnected and synchronized drive.

Thus, it may be seen, that an improved disposable diaper fabricating apparatus 10 and method has been provided by the present invention which will successively form individual prefolded diapers D.

In the drawings and specification, there has been set forth a preferred embodiment of the invention and, although specific terms are employed, they are used in a generic and descriptive sense only and not for purposes of limitation.

What is claimed is:

1. An apparatus for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said apparatus comprising:

means for supplying and positioning an elongate moisture-absorbent interior core including a pad of fibrous material of less width than the width of the core and sheets of cellulosic material on each side of the pad;

means for embossing and securing only the sheets of cellulosic material together along longitudinally-extending lines internal of the sheet edges and adjacent each side of the pad for forming an envelope of the sheets of cellulosic material around the pad;

means cooperating with said core supplying and positioning means for supplying and positioning an elongate fluid-permeable top cover layer on top of the core;

means cooperating with said core supplying and positioning means for supplying and positioning an elongate fluid-impervious bottom cover layer under the core;

means cooperating with said core, top cover layer and bottom cover layer supplying and positioning means for receiving and feeding the superimposed top cover layer, interior core and bottom cover layer along a predetermined longitudinal path of travel;

means cooperating with said supplying and positioning means and said receiving and feeding means for transversely securing the top cover layer and the bottom cover layer together at predetermined longitudinally-spaced intervals to form successively interconnected diapers;

means cooperating with said receiving and feeding means for securing the top cover layer and bottom cover layer together along longitudinal side edges of the successively interconnected diapers; and means cooperating with said receiving and feeding means for transversely severing the successively interconnected diapers along the successive transverse securements to form individual diapers.

2. An apparatus for successively forming disposable diapers, as set forth in claim 1, in which said means for embossing and securing only the sheets of cellulosic material together along longitudinal-extending internal areas of the sheets on each side of the pad comprises a pair of rotating, cooperating roll means positioned generally transversely of the interior core on each side thereof so that the interior core passes therebetween, and at least one of said roll means having embossing collars thereon positioned for engaging the sheets of cellulosic material internally on each side of the pad and embossing the sheets of cellulosic material only against said other roll means for securing the sheets of cellulosic material together along longitudinally-extending internal areas on each side of the pad.

3. An apparatus for successively forming disposable diapers wherein the diaper includes a fluid-permeable top cover layer, a moisture-absorbent interior core under the top cover layer, and a fluid-impervious bottom cover layer under the interior core and secured to the top cover layer along longitudinal and transverse edges thereon, said apparatus comprising:

means for supplying and positioning a plurality of longitudinally-spaced successive elongate moisture-absorbent interior cores;

means cooperating with said core supplying and positioning means for supplying and positioning an elongate fluid-permeable top cover layer on top of the cores;

means cooperating with said core supplying and positioning means for supplying and positioning an elongate fluid-impervious bottom cover layer under the cores;

means cooperating with said core, top cover layer and bottom cover layer supplying and positioning means for receiving and feeding the superimposed top cover layer, interior cores and bottom cover layer along a predetermined longitudinal path of travel;

means cooperating with said supplying and positioning means and said receiving and feeding means for applying a plurality of short, spaced-apart, generally longitudinally-extending, adhesive strips between the top cover layer and the bottom cover layer transversely across the superimposed top cover layer and bottom cover layer at longitudinally-spaced intervals between the cores and extending at least slightly inwardly of the outside ends of the cores for transversely securing the top cover layer and the bottom cover layer together and for securing the cores thereto at longitudinally-spaced intervals by the adhesive strips only to form successively interconnected diapers;

means cooperating with said receiving and feeding means for securing the top cover layer and the bottom cover layer together along longitudinal side edges of the successively interconnected diapers; and means cooperating with said receiving and feeding means for transversely severing the successively interconnected diapers generally medially of the plurality of the longitudinally-extending adhesive strips to form individual diapers.

4. An apparatus for successively forming disposable diapers, as set forth in claim 3, in which said means for applying a plurality of short, spaced-apart, generally longitudinally-extending, adhesive strips between the top cover layer and the bottom cover layer comprises:

an adhesive strip extruding head means positioned adjacent the top face of the bottom cover layer in its path of travel as it is being supplied and positioned by said bottom cover layer supplying and positioning means prior to being positioned under the cores for extruding a plurality of short, spaced-apart, generally longitudinally-extending adhesive strips onto the top face of the bottom cover layer, adhesive supply and conduit means connected with said extruding head means for supplying adhesive thereto, and pump means positioned in said adhesive conduit means including means for intermittently operating said pump means for intermittently pumping and supplying adhesive to said extruding head means for intermittently extruding adhesive strips onto the top face of the bottom cover layer.

5. An apparatus for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said apparatus comprising:

means for supplying and positioning an elongate moisture-absorbent core including a pad of fibrous material of less width than the width of the core and sheets of cellulosic material on each side of the pad;

means for embossing and securing only the sheets of cellulosic material together along longitudinally-extending lines internal of the sheet edges and adjacent each side of the pad for forming an envelope of the sheets of cellulosic material around the pad;

means cooperating with said core supplying and positioning means for supplying and positioning an elongate fluid-permeable top cover layer on top of the core;

means cooperating with said core supplying and positioning means for supplying and positioning an elongate fluid-impervious bottom cover layer under the core;

means cooperating with said core, top cover layer and bottom cover layer supplying and positioning means for receiving and feeding the superimposed top cover layer, interior core and bottom cover layer along a predetermined longitudinal path of travel;

means cooperating with said supplying and positioning means and said receiving and feeding means for applying a plurality of short, spaced-apart, generally longitudinally-extending, adhesive strips between the top cover layer and the bottom cover layer transversely across the superimposed top cover layer and bottom cover layer at longitudinally-spaced intervals for transversely securing the top cover layer and the bottom cover layer together at longitudinally-spaced intervals to form successively interconnected diapers;

means cooperating with said receiving and feeding means for securing the top cover layer and bottom cover layer together along longitudinal side edges of the successively interconnected diapers; and means cooperating with said receiving and feeding means for transversely severing the successively interconnected diapers generally medially of the plurality of the longitudinally-extending adhesive strips to form individual diapers.

6. An apparatus for successively forming disposable diapers, as set forth in claim 5, in which said means for supplying and positioning an elongate moisture-absorbent core includes separate creels for containing separate rolls of continuous cellulosic sheet material and for supplying the sheets of cellulosic material to said diaper forming apparatus;

guide means for receiving the sheets of cellulosic material from said supply creels and for guiding the sheets of cellulosic material into position on each side of the pad of fibrous material, and aligning means cooperating with said guide means for aligning the sheets of cellulosic material as they are being positioned on each side of the pad of fibrous material.

7. An apparatus for successively forming disposable diapers, as set forth in claim 6, in which each of said supply creels comprises a rotatable sheet material roll carrying means for carrying a roll of cellulosic sheet material on each end thereof for positioning one of the rolls in a supply position and the other roll in a reserve position and for being rotatable to position the reserve roll in the supply position when the supply roll is exhausted.

8. An apparatus for successively forming disposable diapers, as set forth in claim 5, in which said means for supplying and positioning an elongate moisture-absorbent core includes means for fiberizing a sheet of wet-pressed, pulp fibers into individual fibers and forming individual, longitudinally spaced-apart pads of such fibers directly onto the continuous sheet of cellulosic material positioned under the pad.

9. An apparatus for successively forming disposable diapers, as set forth in claim 8, in which said fiberizing and pad forming means comprises:

generally enclosed, stationary chamber means having an open bottom and a slot in an upper portion thereof to receive a sheet of wet-pressed pulp fibers, rotatably mounted and driven fiberizing means mounted in the upper portion of said chamber means for contacting the sheet of wet-pressed pulp fibers and fiberizing the sheet into substantially individual fibers, driven, longitudinally moving conveyor belt means for receiving on the top surface thereof the sheet of cellulosic material to be positioned under the spaced-apart pads and having longitudinally-spaced groups of small perforations therein along the length thereof corresponding to the desired configuration and spacing of the fiber pads being formed and being positioned for movement along said open bottom end of said chamber means directly below said fiberizing means and cooperating with said chamber means for forming an enclosed pad forming area in a lower portion of said chamber means and for receiving the fiberized fibers on the upper surface thereof and of the sheet of cellulosic material thereon and conveying the fiberized fibers and the sheet of cellulosic material out of said chamber means, and stationary vacuum means positioned at the lower surface of said belt means and directly below said chamber means for creating a vacuum through said groups of perforations in said moving belt means and through the sheet of cellulosic material being carried thereon for causing said fibers to be pulled to said groups of perforations to form individual, spaced-apart pads on the sheet of cellulosic material and on said moving belt means over said groups of perforations and within said lower portion of said chamber means for being conveyed by said belt means out of said chamber means after formation thereof.

10. An apparatus for successively forming disposable diapers as set forth in claim 8, in which said apparatus further includes cutting means cooperating with said positioning means for partially cutting the elongate core transversely thereof between the spaced-apart pads of fibers prior to the positioning of the top and bottom cover layers by said supplying and positioning means, and drafting means cooperating with said top and bottom cover layer positioning means and said receiving and feeding means for drafting the partially cut elongate core to separate the elongate core into longitudinally spaced-apart individual cores as the top and bottom cover layers are positioned on each side thereof by said supplying and positioning means, and said means for applying the plurality of adhesive strips cooperates with said drafting means to position the adhesive strips between the bottom cover layer and the top cover layer at the spacing between the individually formed core members.

11. An apparatus for successively forming disposable diapers, as set forth in claim 5, in which the bottom cover layer is wider than the diapers being formed so that the bottom cover layer includes outer longitudinal edge portions extending outwardly from each side of the successively interconnected diapers when the bottom cover layer is positioned under the core, and in which said means for securing the top cover layer and the bottom cover layer together along the longitudinal side edges of the successively interconnected diapers comprises adhesive applying means cooperating with said receiving and feeding means for applying continuous longitudinally-extending lines of adhesive onto the top cover layer adjacent the outer longitudinal edges of the successively interconnected diapers, and folding means for folding the outer extending longitudinal edge portions of the bottom cover layer over the top of the top cover layer and over the longitudinally-extending adhesive lines for securing the folded over portions of the bottom cover layer to the top cover layer.

12. An apparatus for successively forming disposable diapers, as set forth in claim 5, in which said apparatus further includes means cooperating with said receiving and feeding means for longitudinally folding the successively interconnected diapers along longitudinally-extending fold lines so that side portions of the successively interconnected diapers are folded inwardly over the central portion of the successively interconnected diapers and then folded outwardly back over themselves to form prefolded successively interconnected diapers.

13. An apparatus for successively forming disposable diapers, as set forth in claim 12, in which said folding means comprises a longitudinally-extending folding plate positioned in the path of travel of the successively interconnected diapers for engaging the central portion of the successively interconnected diaper and holding this central portion against any folding action and allowing the folding over of the side portions of the successively interconnected diapers around the edges thereof and over the central portion, and longitudinally-extending, inwardly tapering folding bars positioned generally above the folding plate for engaging the side portions of the successively interconnected diapers and causing these side portions to fold inwardly over the central portion and around said folding plate and then outwardly back over themselves to form prefolded interconnected diapers.

14. An apparatus for successively forming disposable diapers, as set forth in claim 5, in which said apparatus further includes means cooperating with said receiving and feeding means for applying a pair of elongate securing tabs having adhesive on one face thereof to the outer longitudinal edges, respectively, of the bottom cover layer.

15. An apparatus for successively forming disposable diapers, as set forth in claim 5, in which said transverse severing means comprises:

a pair of rotating rolls positioned transversely on each side of the traveling, successively interconnected diapers, one of said rolls having cutting blade means and the other of said roll means having cooperating anvil means for cutting the successively interconnected diapers generally medially of the plurality of longitudinally-extending adhesive strips to form individual diapers when said blade means and said anvil means are rotated into engagement with each other by said rotating rolls.

16. An apparatus for successively forming disposable diapers, as set forth in claim 5, in which said apparatus further includes means cooperating with said receiving and feeding means and positioned subsequent to said transverse severing means for successively receiving the individual diapers and counting a predetermined number of such diapers and separating the predetermined number of such diapers for packaging.

17. An apparatus for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said apparatus comprising:

means for supplying and positioning an elongate moisture-absorbent core including pads of fibrous material of less width than the width of the core and sheets of cellulosic material on each side of the pads and including means for fiberizing a sheet of wet-pressed, pulp fibers into individual fibers and forming individual, longitudinally spaced-apart pads of such fibers onto the continuous sheet of cellulosic material positioned under the pads;

means for embossing and securing the sheets of cellulosic material together along longitudinally-extending areas on each side of the spaced-apart pads for forming an envelope of the sheets of cellulosic material around the spaced-apart pads;

cutting means cooperating with said core positioning means for partially cutting the elongate core transversely thereof between the spaced-apart pads, and cooperating drafting means for drafting the partially cut elongate core to separate the elongate core into longitudinally spaced-apart individual cores;

means cooperating with said core supplying and positioning means and cutting and drafting means for supplying and positioning an elongate fluid-permeable top cover layer on top of the spaced-apart individual cores;

means cooperating with said core supplying and positioning means and cutting and drafting means for supplying and positioning an elongate fluid-impervious bottom cover layer under the individual spaced-apart cores;

means cooperating with said core, top cover layer and bottom cover layer supplying and positioning means for receiving and feeding the superimposed top cover layer, interior cores and bottom cover layer along a predetermined longitudinal path of travel;

means cooperating with said supplying and positioning means and said receiving and feeding means for applying a plurality of short, spaced-apart, generally longitudinally-extending, adhesive strips between the top cover layer and the bottom cover layer transversely across the superimposed top cover layer and bottom cover layer at longitudinally-spaced intervals between the individual spaced-apart cores for transversely securing the top cover layer and bottom cover layer together to form successively interconnected diapers;

means cooperating with said receiving and feeding means for securing the top cover layer and bottom cover layer together along longitudinal side edges of the successively interconnected diapers; and means cooperating with said receiving and feeding means for transversely severing the successively interconnected diapers generally medially of the plurality of longitudinally-extending adhesive strips to form individual diapers.

18. An apparatus for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said apparatus comprising:

means for supplying and positioning an elongate moisture-absorbent core including pads of fibrous material of less width than the width of the core and sheets of cellulosic material on each side of the pads and including means positioned directly over one of the sheets of cellulosic material which is to be positioned under the pad for fiberizing a sheet of wet-pressed pulp fibers into individual fibers and forming individual, longitudinally spaced-apart pads of such fibers directly onto the continuous sheet of cellulosic material positioned under the pads;

means for embossing and securing the sheets of cellulosic material together along longitudinally-extending areas of each side of the spaced-apart pads for forming an envelope of the sheets of cellulosic material around the spaced-apart pads;

cutting means cooperating with said core positioning means for partially cutting the elongate core transversely thereof between the spaced-apart pads, and cooperating drafting means for drafting the partially cut elongate core to separate the elongate core into longitudinally spaced-apart individual cores;

means cooperating with said core supplying and positioning means and cutting and drafting means for supplying and positioning an elongate fluid-permeable top cover layer on top of the spaced-apart individual cores;

means cooperating with said core supplying and positioning means and cutting and drafting means for supplying and positioning an elongate fluid-impervious bottom cover layer under the individual spaced-apart cores;

means cooperating with said core, top cover layer and bottom cover layer supplying and positioning means for receiving and feeding the superimposed top cover layer, interior cores and bottom cover layer along a predetermined longitudinal path of travel;

means cooperating with said supplying and positioning means and said receiving and feeding means for applying a plurality of short, spaced-apart, generally longitudinally-extending, adhesive strips between the top cover layer and the bottom cover layer transversely across the superimposed top cover layer and bottom cover layer at longitudinally-spaced intervals between the individual spaced-apart cores for transversely securing the top cover layer and bottom cover layer together to form successively interconnected diapers;

means cooperating with said receiving and feeding means for securing the top cover layer and bottom cover layer together along longitudinal side edges of the successively interconnected diapers;

means cooperating with said receiving and feeding means for longitudinally folding the successively interconnected diapers along longitudinally-extending fold lines so that side portions of the successively interconnected diapers are folded inwardly over the central portion thereof and then folded outwardly back over themselves to form prefolded successively interconnected diapers;

means cooperating with said receiving and feeding means for applying a pair of elongate securing tabs having adhesive on one face thereof to the outer longitudinal edges, respectively, of the bottom cover layer;

means cooperating with said receiving and feeding means for transversely severing the successively interconnected diapers generally medially of the plurality of longitudinally-extending adhesive strips to form individual diapers; and means cooperating with said receiving and feeding means and positioned subsequent to said transverse severing means for successively receiving the individual diapers and counting a predetermined number of such diapers and separating the predetermined number of such diapers for packaging.

19. A method for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said method comprising the successive steps of:

supplying and positioning an elongate moisture-absorbent interior core including a pad of fibrous material of less width than the width of the core and sheets of cellulosic material on each side of the pad;

embossing and securing only the sheets of cellulosic material together along longitudinally-extending lines internal of the sheet edges and adjacent each side of the pad for forming an envelope of the sheets of cellulosic material around the pad;

supplying and positioning an elongate fluid-permeable top cover layer on top of the core and an elongate fluid-impervious bottom cover layer under the core;

feeding the superimposed top cover layer, interior core and bottom cover layer along a predetermined longitudinal path of travel;

transversely securing the top cover layer and bottom cover layer together at predetermined longitudinally-spaced intervals to form successively interconnected diapers;

securing the top cover layer and bottom cover layer together along longitudinal side edges of the successively interconnected diapers; and transversely severing the successively interconnected diapers along the successive transverse securements to form individual diapers.

20. A method for successively forming disposable diapers wherein the diaper includes a fluid-permeable top cover layer, a moisture-absorbent interior core under the top cover layer, and a fluid-impervious bottom cover layer along longitudinal and transverse edges thereof, said method comprising the successive steps of:

supplying and positioning a plurality of longitudinally-spaced successive elongate moisture-absorbent interior cores;

supplying and positioning an elongate fluid-permeable top cover layer on top of the cores and an elongate fluid-impervious bottom cover layer under the cores;

feeding the superimposed top cover layer, interior cores and bottom cover layer along a predetermined longitudinal path of travel;

applying a plurality of short, spaced-apart, generally longitudinally-extending, adhesive strips between the top cover layer and the bottom cover layer transversely across the superimposed top cover layer and bottom cover layer at longitudinally-spaced intervals between the cores and extending at least slightly inwardly of the outside ends of the cores for transversely securing the top cover layer and bottom cover layer together and for securing the cores thereto at longitudinally-spaced intervals by the adhesive strips only to form successively interconnected diapers;

securing the top cover layer and the bottom cover layer together along longitudinal side edges of the successively interconnected diapers; and transversely severing the successively interconnected diapers generally medially of the plurality of the longitudinally-extending adhesive strips to form individual diapers.

21. A method for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereof, said method comprising the successive steps of:

supplying and positioning an elongate moisture-absorbent core including a pad of fibrous material of less width than the width of the core and sheets of cellulosic material on each side of the pad;

embossing and securing only the sheets of cellulosic material together along longitudinally-extending lines internal of the sheet edges and adjacent each side of the pad for forming an envelope of the sheets of cellulosic material around the pad;

supplying and positioning an elongate fluid-permeable top cover layer on top of the core and an elongate fluid-impervious bottom cover layer under the core;

feeding the superimposed top cover layer, interior core and bottom cover layer along a predetermined longitudinal path of travel;

applying a plurality of short, spaced-apart, generally longitudinally-extending, adhesive strips between the top cover layer and the bottom cover layer transversely across the superimposed top cover layer and bottom cover layer at longitudinally-spaced intervals for transversely securing the top cover layer and the bottom cover layer together at longitudinally-spaced intervals by the adhesive strips only to form successively interconnected diapers;

securing the top cover layer and the bottom cover layer together along longitudinal side edges of the successively interconnected diapers; and transversely severing the successively interconnected diapers generally medially of the plurality of the longitudinally-extending adhesive strips to form individual diapers.

22. A method for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said method comprising the successive steps of:

supplying and positioning an elongate moisture-absorbent core including pads of fibrous material of less width than the width of the core and sheets of cellulosic material on each side of the pad and including fiberizing a sheet of wet-pressed, pulp fibers into individual fibers and forming individual, longitudinally spaced-apart pads of such fibers onto the continuous sheet of cellulosic material positioned under the pads;

embossing and securing the sheets of cellulosic material together along longitudinally-extending areas on each side of the spaced-apart pads for forming an envelope of the sheets of cellulosic material around the spaced-apart pads;

partially cutting the elongate core transversely thereof between the spaced-apart pads and drafting the partially cut elongate core to separate the elongate core into longitudinally spaced-apart individual cores;

supplying and positioning an elongate fluid-permeable top cover layer on top of the spaced-apart individual cores and an elongate fluid-impervious bottom cover layer under the individual spaced-apart cores;

feeding the superimposed top cover layer, interior cores and bottom cover layer along a predetermined longitudinal path of travel;

applying a plurality of short, spaced-apart, generally longitudinally-extending, adhesive strips between the top cover layer and the bottom cover layer transversely across the superimposed top cover layer and bottom cover layer at longitudinally-spaced intervals between the individually spaced-apart cores for transversely securing the top cover layer and bottom cover layer together to form successively interconnected diapers;

securing the top cover layer and bottom cover layer together along longitudinal side edges of the successively interconnected diapers; and transversely severing the successively interconnected diapers generally medially of the plurality of longitudinally-extending adhesive strips to form individual diapers.

23. A method for successively forming disposable diapers wherein the diaper includes a fluid-permeable top cover layer, a moisture-absorbent interior core under the top cover layer and including a pad of fibrous material and sheets of cellulosic material on each side of the pad, and a fluid-impervious bottom cover layer under the interior core and secured to the top cover layer along longitudinal and transverse edges thereon, said method comprising the successive steps of:

supplying and positioning an elongate moisture-absorbent core including pads of fibrous material of less width than the width of the core and sheets of cellulosic material on each side of the pads and including fiberizing a sheet of wet-pressed pulp fibers into individual fibers and forming individual, longitudinally spaced-apart pads of fibers directly over and onto the sheet of cellulosic material positioned under the pads;

embossing and securing the sheets of cellulosic material together along longitudinally-extending areas on each side of the spaced-apart pads for forming an envelope of the sheets of cellulosic material around the spaced-apart pads;

partially cutting the elongate core transversely thereof between the spaced-apart pads and drafting the partially cut elongate core to separate the elongate core into longitudinally spaced-apart individual cores;

supplying and positioning an elongate fluid-permeable top cover layer on top of the spaced-apart individual cores and an elongate fluid-impervious bottom cover layer under the individual spaced-apart cores;

feeding the superimposed top cover layer, interior cores and bottom cover layer along a predetermined longitudinal path of travel;

applying a plurality of short, spaced-apart, generally longitudinally extending, adhesive strips between the top cover layer and the bottom cover layer transversely across the superimposed top cover layer and bottom cover layer at longitudinally-spaced intervals between the individually spaced-apart cores for transversely securing the top cover layer and bottom cover layer together to form successively interconnected diapers;

securing the top cover layer and bottom cover layer together along longitudinal side edges of the successively interconnected diapers;

longitudinally folding the successively interconnected diapers along longitudinally-extending fold lines so that side portions of the successively interconnected diapers are folded inwardly over the central portion thereof and then folded outwardly back over themselves to form prefolded successively interconnected diapers;

applying a pair of elongate securing tabs having adhesive on one face thereof to the outer longitudinal edges, respectively, of the bottom cover layer;

transversely severing the successively interconnected diapers generally medially of the plurality of longitudinally-extending adhesive strips to form individual diapers; and counting a predetermined number of cut and formed diapers and separating the predetermined number of such diapers for packaging.

24. A method for successively forming disposable diapers, as set forth in claim 23, in which the bottom cover layer is wider than the diapers being formed so that the bottom cover layer includes outer longitudinal edge portions extending outwardly from each side of the successively interconnected diapers when the bottom cover layer is positioned under the core, and in which said step of securing the top cover layer and bottom cover layer together along the longitudinal side edges of the successively interconnected diapers comprises:

applying continuous longitudinally-extending lines of adhesive onto the top cover layer adjacent the outer longitudinal edges of the successively interconnected diapers; and folding the outer extending longitudinal edge portions of the bottom cover layer over the top of the top cover layer and over the longitudinally-extending adhesive lines for securing the folded over portion of the bottom cover layer to the top cover layer.

* * * * *